United States Patent
Rice et al.

(10) Patent No.: US 6,896,366 B2
(45) Date of Patent: May 24, 2005

(54) GOGGLES

(75) Inventors: John Ronald Rice, Upper Tean (GB); Mark Andrew Walker, Aston Lodge Stone (GB)

(73) Assignee: NPF Limited, Birmingham (GB)

( * ) Notice: Subject to any disclaimer, the term of this patent is extended or adjusted under 35 U.S.C. 154(b) by 0 days.

(21) Appl. No.: 10/828,730

(22) Filed: Apr. 21, 2004

(65) Prior Publication Data

US 2005/0036100 A1 Feb. 17, 2005

(30) Foreign Application Priority Data

Aug. 14, 2003 (GB) ............................................. 0319058

(51) Int. Cl.⁷ .............................................. G02C 11/08
(52) U.S. Cl. .............................. 351/62; 351/158; 2/437
(58) Field of Search .......................... 351/41, 62, 158;
2/435–437, 6.3, 171.3, 906, 909, DIG. 1;
128/857, 858, 204.23, 205.11

(56) References Cited

U.S. PATENT DOCUMENTS

| | | | |
|---|---|---|---|
| 3,517,393 A | * | 6/1970 | Beauchef ..................... 351/62 |
| 3,556,645 A | * | 1/1971 | Heilman ..................... 351/155 |
| 3,825,953 A | | 7/1974 | Hunter |
| 4,150,443 A | | 4/1979 | McNeilly |
| 4,443,893 A | | 4/1984 | Yamamoto |
| 4,996,981 A | | 3/1991 | Elenewski et al. |
| 5,029,342 A | * | 7/1991 | Stein et al. ..................... 2/8 |
| 5,148,550 A | | 9/1992 | Hodgkinson et al. |
| 5,371,804 A | | 12/1994 | Bauer |
| 5,428,688 A | | 6/1995 | Becker et al. |
| 5,452,480 A | | 9/1995 | Ryden |
| 5,533,500 A | | 7/1996 | Her-Mou |
| 5,966,746 A | | 10/1999 | Reedy et al. |
| 6,038,707 A | | 3/2000 | Ryden et al. |
| 6,047,411 A | | 4/2000 | Ryden et al. |
| 6,094,751 A | | 8/2000 | Parks |
| 6,257,235 B1 | | 7/2001 | Bowen |
| 6,363,528 B1 | | 4/2002 | Cyr |
| 6,704,944 B2 | * | 3/2004 | Kawainshi et al. ............ 2/436 |
| 2002/0166159 A1 | | 11/2002 | Kawanishi et al. |

FOREIGN PATENT DOCUMENTS

| | | |
|---|---|---|
| DE | 28 21 121 B1 | 5/1978 |
| GB | 2 165 721 A | 4/1986 |
| WO | WO 95/13689 A1 | 5/1995 |

* cited by examiner

Primary Examiner—Huy Mai
(74) Attorney, Agent, or Firm—Vedder Price Kaufman & Kammholz, P.C.

(57) ABSTRACT

A goggle, for use, for example, in paintball, comprises a lens 12, a body structure 14 for the lens and a strap 16. The body structure defines an ocular chamber 34 that covers the wearer's eyes, and an exhalation chamber 36 that covers the wearer's nose and mouth. An inlet plenum channel 42 leads from an inlet chamber 44 in the front of the goggle 10 up to the lower edge of the lens 12, and a fan 46 in the plenum channel 42 blows air from the inlet upwards across the inner surface of the lens 12. Air exhaled by the wearer leaves the exhalation chamber through outlet apertures 56 in the bottom of the mask, and is therefore directed away from the duct inlet chamber 44.

43 Claims, 11 Drawing Sheets

GOGGLES

FIELD OF THE INVENTION

The present invention relates to goggles, and is especially suitable for sports goggles and in particular paintball goggles.

BACKGROUND OF THE INVENTION

Goggle systems for paintball generally consist of a number of items that are over and above normal eye protection. The main requirement of a paintball goggle system is that it protects the user from single or multiple strikes from paintballs that are fired from a paintball marker. Typically, the paintballs are fired at a velocity of 300 feet/second (91.44 m/s) with impact energy of 9.9 foot lbs. (13.42 Joules). For testing purposes, the loads are higher, as specified in ASTM guidelines. The goggle system must perform certain functions: retention on the user's head, maintaining lens integrity to prevent it from popping out under load, and face and ear protection from paintball strikes.

In addition, the ocular chamber is preferably ventilated to allow air to flow across the lens and face to remove condensates. However, due to the nature of the protection required, the venting generally consists of apertures that must prevent a whole paintball or a broken paintball from entering the ocular chamber with sufficient energy to cause eye injury. Another problem with the ventilation is that paintball is played relatively statically, and therefore forced airflow though the goggle is relatively small when compared to skiing, for example, or motocross, or any activity that will provide a ram air effect due to movement. The same problem of a lack of ram air can also occur in these other sports during periods where the wearer is temporarily inactive, such as when the goggle is first put on, or during a break in activity, when it is important that the goggle does not become fogged.

It is a problem with some known goggle systems that the condensation that builds up within the goggle will precipitate onto the lens surface and cause fogging. The key element in this fogging is the dew point of the air, and the fogging can occur in a warm or cold environment, dependent on the relative humidity and the temperature difference between the saturated air and the lens surfaces. Also, in situations where the user generates a high amount of moisture due to sweating, there is little or no airflow present sweating alone can cause fogging.

A number of solutions to the problem of fogging in paintball goggles have been tried and are used, as will now be described.

One known solution to fogging of paintball goggles is to provide an anti-fog moisture-absorbing coating on the inner surface of a single lens. This coating absorbs the moisture that precipitates on the surface, and, in so doing, removes the very small droplets of water that appear as fog on the lens surface, thus maintaining the optical clarity of the lens. However, a disadvantage of this type of coating is that the coating can reach saturation where it will no longer absorb water, and the water can only condense on the lens surface. Once the lens has been in an atmosphere with less humidity, the process will reverse and the moisture will evaporate from the lens coating. Further problems with this type of coating are that the coating has a limited use in relation to the amount of moisture it can absorb; the coating itself is very fragile and prone to scratching or marking; and, should, the coating become damaged, its optical properties and anti-fogging properties are substantially reduced.

Another solution is the use of double lenses, which generate a thermal barrier within the lens structure working on the same principle as double-glazing. The inner lens surface is warmer than the outer lens, and, because the inner lens remains warm, the moisture-laden air will not condense onto the lens surface to cause fogging. A problem with double lenses is that the lenses must remain hermetically sealed to prevent any moisture from entering between them, or condensation will form between the lenses. Another problem that can be associated with double lenses is that the lens structure becomes thicker and, due to its relatively close proximity to the eyes, a distortion can occur causing parallax, which affects the optical properties of the lens.

Some manufacturers have attempted to insert fans within the goggle system in the brow area of the goggle; these are successful to a degree. However, these systems have not provided a completely satisfactory solution to the problem of fogging, and fan-assisted goggles have often required that they be backed up with anti-fog or thermal lenses to ensure adequate performance.

SUMMARY OF THE INVENTION

Accordingly, the present invention provides a goggle comprising a lens; a body structure supporting the lens and defining therewith an ocular chamber for extending over the eyes of a wearer, wherein the body structure further defines an exhalation chamber for extending over at least one of the nose and mouth of a wearer; and an inlet chamber, at least part of which is arranged to be in front of the exhalation chamber in use. The goggle further comprises: a fan located in the inlet chamber, and air deflection means located between the inlet chamber and the exhalation chamber, arranged to deflect air from the fan upwards into the ocular chamber. Such an arrangement helps to prevent moisture from exhaled air reaching the lens, where it can cause fogging. It also allows better control of the airflow in the ocular chamber, since it is not affected by the flow of exhaled air from the wearer's nose or mouth.

Preferably, the air deflection means is arranged to direct air across the lens in an upward direction. However, it can be arranged to direct air in other directions, such as outwards from a central nose region.

Preferably, the body structure defines an ocular chamber outlet at the upper side of the ocular chamber through which air entering the ocular chamber from the air inlet chamber can escape. Alternatively, or in addition, the outlet can be at the sides of the ocular chamber. The ocular chamber outlet preferably has a covering thereover having apertures therethrough which are no greater than 15 mm$^2$ so as to prevent debris from entering the ocular chamber. More preferably the apertures are no greater than 10 mm$^2$.

Preferably, the inlet chamber has an inlet through which air can enter the inlet chamber from the exterior of the goggle, and the inlet is formed in the front of the goggle. This helps to ensure that the air entering the inlet has not been either exhaled by the wearer or recently passed over the head of the wearer, thereby reducing the amount of warm sweat-carrying air entering the inlet.

Preferably, the fan is positioned in a part of the inlet chamber in front of the exhalation chamber. More preferably, the fan is positioned so as to be, in use, in front of the wearer's nose or mouth.

Preferably, the inlet is below the lens, and the deflection means is arranged to direct air upwards from the inlet chamber to the inner surface of the lens. More preferably, the exhalation chamber has an exhaled air outlet arranged to be, in use, below the inlet, and the exhaled air outlet is preferably arranged to direct exhaled air downwards away from the inlet.

Preferably, the deflection means partially defines a channel having an outlet that is adjacent to the lens. This helps to promote the smooth laminar flow of air across the lens. For the same reason, the air deflection means is preferably arranged to direct air in a direction substantially parallel to the lens so that the air flows across the inner surface of the lens, and the ocular chamber outlet is preferably positioned adjacent to the lens so that air flowing across the lens can flow on through the outlet.

Preferably, the shape of the air deflection means and the fan speed are arranged to direct the air so that it flows across the lens in a substantially laminar manner. The laminar air flow can be controlled in a relatively easy manner because the ocular chamber is separate from the exhalation chamber in which the airflow will be affected by the breath of the wearer. Preferably, the air deflection means is arranged to direct the air flow in the ocular chamber so that it occurs mostly in a region of the ocular chamber adjacent to the lens and spaced from the wearer's face.

The present invention further provides a goggle comprising a lens, a body structure supporting the lens and defining an air inlet means arranged to direct air from the exterior of the goggle across an inner surface of the lens, a fan located in the air inlet means for causing air to flow through the air inlet means, and a drive system for driving the fan wherein the drive system includes a controller arranged to switch the fan repeatedly between an on state and an off state so as to control the amount of air directed across the lens, and to control the timing of the switching so that each time the fan is switched to the on state it remains in that state for at least a predetermined time to allow for airflow across the lens to reach a steady state.

Preferably, the controller is arranged to vary the length of the periods for which the fan is in at least one of the on state and the off state so as to vary the amount of airflow across the lens.

Preferably, the drive system includes a sensing means arranged to sense a condition that will affect fogging of the lens, and the controller is arranged to control operation of the fan in response to a signal from the sensing means.

The present invention further provides a goggle comprising a lens, a body structure supporting the lens and defining an air inlet means arranged to direct air from the exterior of the goggle across an inner surface of the lens, a fan located in the air inlet means for causing air to flow through the air inlet means, and a drive system for driving the fan wherein the drive system includes a sensing means arranged to sense a condition that will affect fogging of the lens, and a controller arranged to control operation of the fan in response to a signal from the sensing means.

The sensing means preferably includes a temperature sensor arranged to measure the temperature in a region close to the lens, and also preferably includes a humidity sensor arranged to measure the humidity of air in a region within the goggle close to the lens.

The goggle preferably further comprises a strap formed from a piece of elastomeric material.

The present invention further provides a goggle comprising a lens, a body structure supporting the lens and a strap connected to the body structure wherein the strap is formed from a piece of elastomeric material. Preferably, the strap is connected to the body structure by means of pivoting connectors. Preferably, the strap has a number of apertures formed therethrough. More preferably, the strap is sufficiently flexible to be nonadjustable.

BRIEF DESCRIPTION OF THE DRAWINGS

Preferred embodiments of the present invention will now be described by way of example only with reference to the accompanying drawings, in which.

DETAILED DESCRIPTION OF THE PREFERRED EMBODIMENTS

Figure 1:
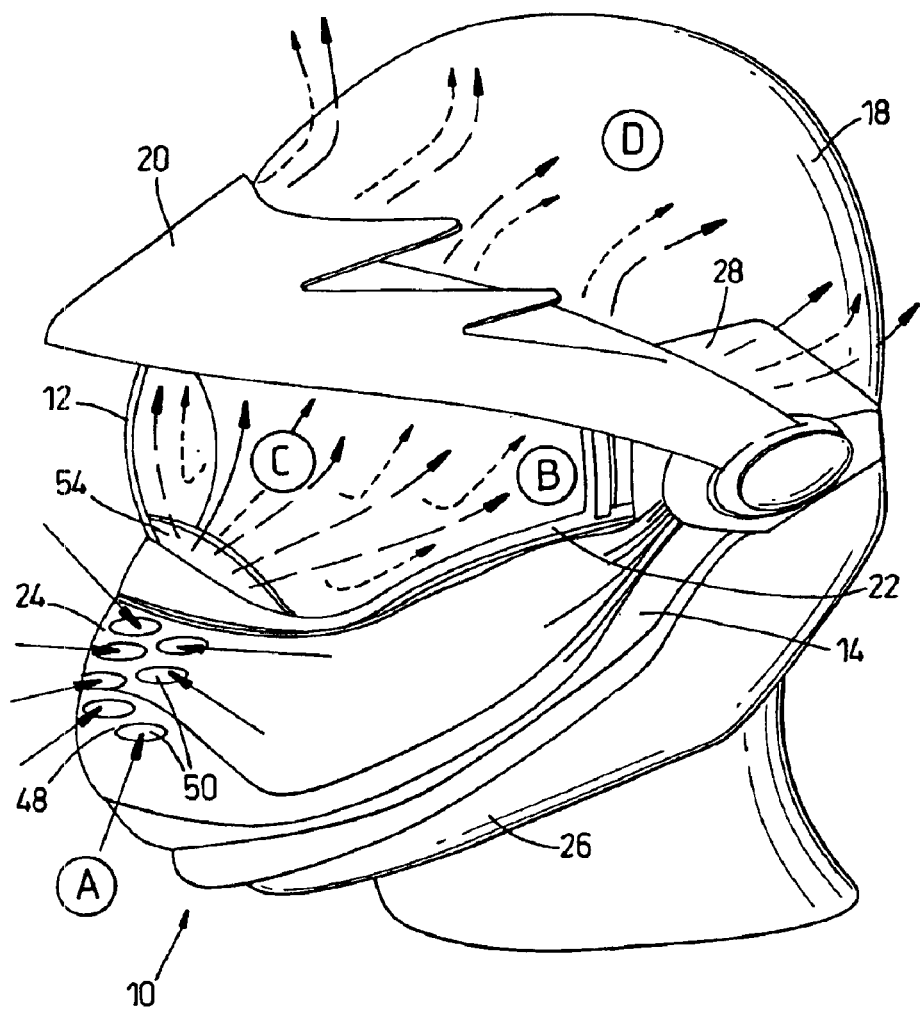
FIG. 1 is a front perspective view of a goggle according to a first embodiment of the invention in use by a wearer.
Figure 2:
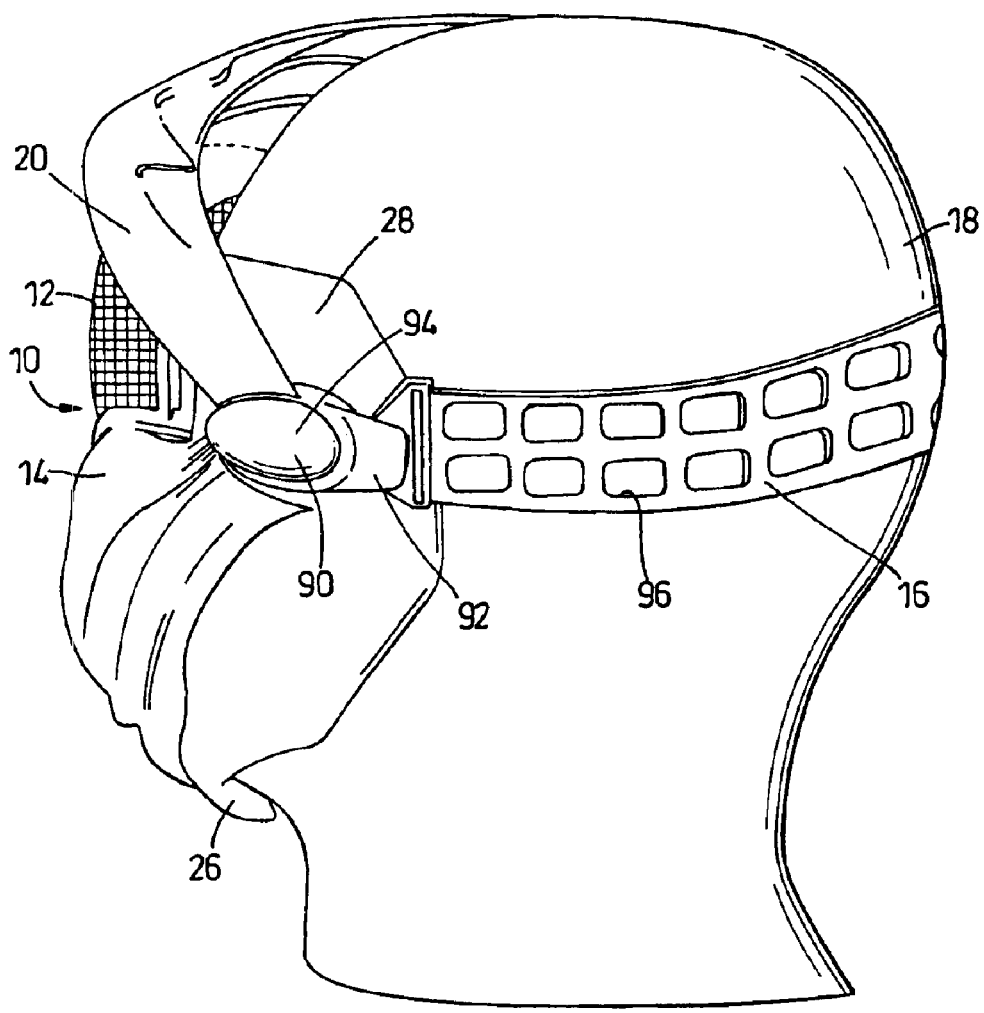
FIG. 2 is a rear perspective view of the goggle and wearer of FIG. 1.
Figure 3:
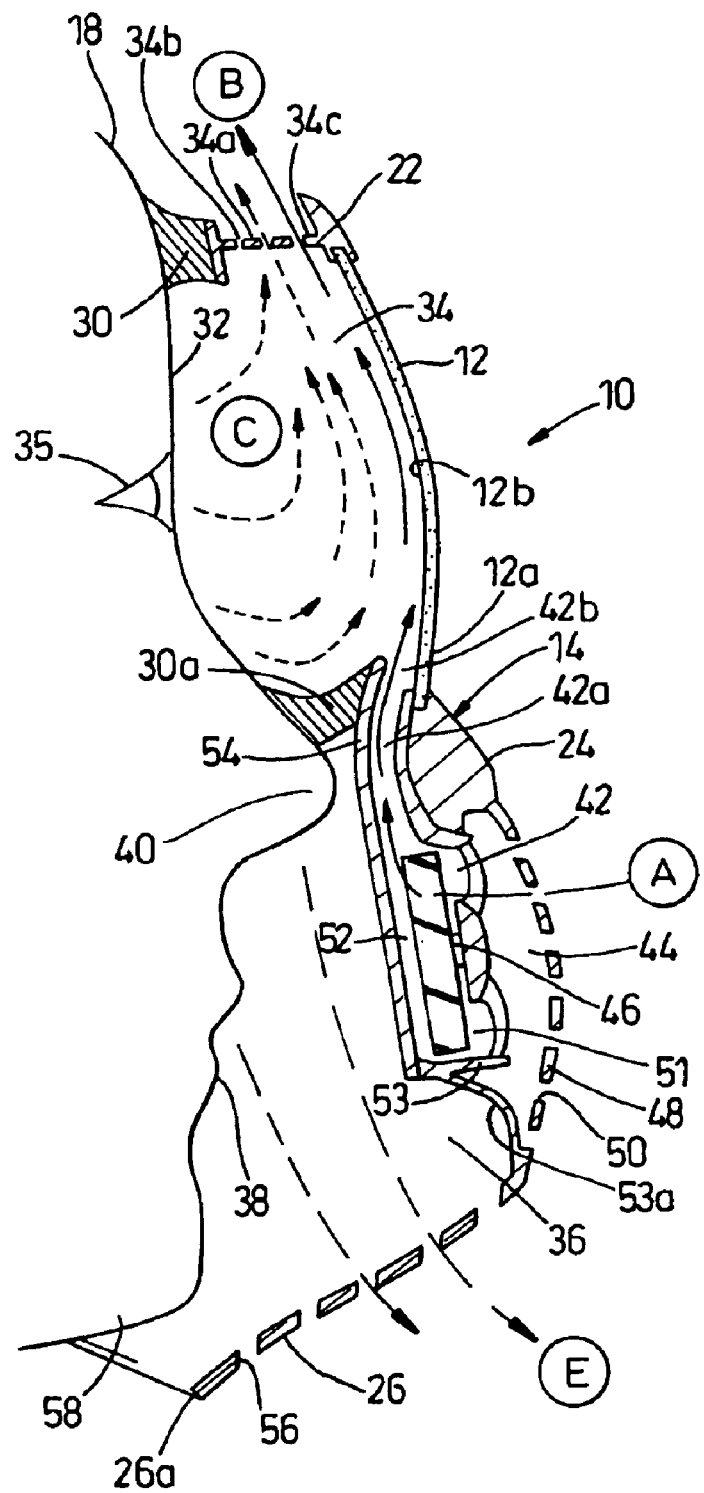
FIG. 3 is a vertical section through the goggle of FIG. 1.

Referring to FIGS. 1 through 3, a goggle system 10 comprises a one-piece single lens 12 supported in a molded plastic body 14 that can be molded as a number of separate parts, a strap 16 arranged to pass around the rear of a wearer's head 18 for securing the goggle in position on the head 18 of the wearer and a visor 20.

The body 14 is of a semirigid, flexible construction such that it can follow, and fit to, the contours of the wearer's face when it is worn. The body 14 comprises a lens frame portion 22, which surrounds and supports the lens 12, a nose protection portion 24, a jaw protection portion 26 and ear protection portions 28 on either side. A gasket 30, shown also in FIG. 6, extends around the inside of the frame portion 22 and is arranged to rest against the wearer's face 32 around his eyes when the goggle is in use, thereby providing the main location for the goggle 10. When in use, the lens 12, the lens supporting portion 22 of the body 14 and the gasket 30 form a first chamber in the form of an ocular chamber 34 in front of the wearer's eyes 35 and behind the lens 12. The nose protection portion 24 and jaw protection portion 26 define an exhalation chamber 36 in front of the wearer's mouth 38 and nose 40, the top of which is defined by the lower portion 30a of the gasket 30, which fits over the bridge of the wearer's nose 40 and provides a seal between the ocular chamber 34 and the nose and mouth chamber 36.

In the center of the body 14 below the lens 12, an air inlet means in the form of a duct or plenum channel 42 is formed. This plenum channel 42 has a broad inlet chamber 44 with a fan 46 mounted in it driven by an electric motor 47 (see FIG. 8). The fan is arranged to rotate about a substantially horizontal axis, drawing air in from the forward direction and propelling it in a rearward direction towards the exhalation chamber 36. The front of the inlet chamber 44 is formed by an inlet cover portion 48 of the body that has a number of apertures 50 formed through it. In the back 52 of the inlet chamber, a fan chamber 51 is formed, surrounded by a fan chamber wall 53 and opening at its front into the inlet chamber 44. From the back of the fan chamber 51, an upper part 42a of the plenum channel 42 extends upwards into the ocular chamber 34. The back of the plenum channel 42 is formed by a substantially vertical crescent-shaped air diverter plate 54 that separates the plenum channel 42 from the nose and mouth chamber 36 and which deflects air from the fan 46 upwards towards the ocular chamber 34. The back 54a of this diverter plate 54 carries the lower part of the gasket 30, which seals against the wearer's face in the region over his nose 40. The front of the upper part 42a of the plenum channel 42 is formed by the lens frame portion 22 of the body 14. The upper part 42a of the plenum channel 42 is therefore a wide and flat and crescent-shaped opening into the ocular chamber 34 adjacent to the lower edge 12a of the lens 12. The lens 12 is convex, as can be seen in FIG. 3, and the top end 42b of the plenum channel 42 directs air traveling along it in a direction substantially parallel to the plane of the lower edge 12a of the lens 12.

It will be appreciated that as the plenum channel 42 turns through a substantially right angle bend between the inlet chamber 44 and the upper part 42a, there is no straight-line path by means of which objects such as paintball parts or stones can enter the ocular chamber 34 to reach the wearer's eyes. This is an important safety requirement.

The bottom of the exhalation chamber 36 is formed by part of the jaw protection portion 26 of the body 14. This has a number of apertures 56 through it to allow air to enter the exhalation chamber 36 for the wearer to breath in, and to allow air exhaled by the wearer to escape. A web 53a extends between the region where the jaw protection portion 26 is joined to the inlet cover portion 48 and the lower edge of the fan chamber wall 53. The web 53a therefore forms a seal preventing air from flowing from the exhalation chamber around the lower edge of the fan chamber wall 53 into the inlet chamber 44.

The top of the lens frame portion 22 above the lens 12 forms a top wall 34a of the ocular chamber 34 that extends substantially perpendicular to the lens 12 and is substantially horizontal in use, as can best be seen in FIG. 3. This top wall 34a extends across the whole width of the lens 12 and has apertures 34b through it over the whole of its length. The size of these apertures is chosen, in accordance with ASTM guidelines, to prevent paintball fragments or other debris from entering the ocular chamber where they might damage the wearer's eyes. The top wall 34a is level, in the vertical direction, with the top of the gasket 30 and is therefore spaced from the wearer's head 18 by the thickness of the gasket 30. The apertures 34b extend forward to the front edge 34c of the top wall 34a, substantially as far as the edge of the lens 12, so that air traveling upwards over the surface of the lens can pass out through the apertures 34b without a substantial change of direction.

Figure 6:
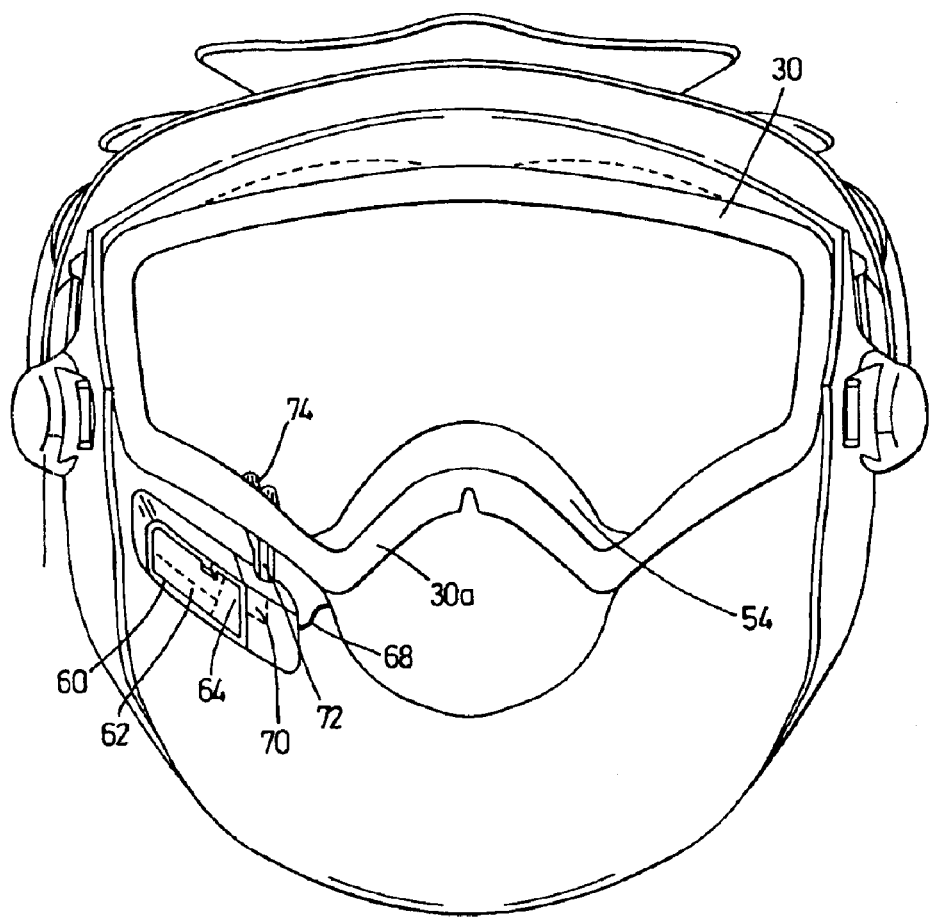
FIG. 6 is a partially cut-away front view of the goggle of FIG. 1.
Figure 8:
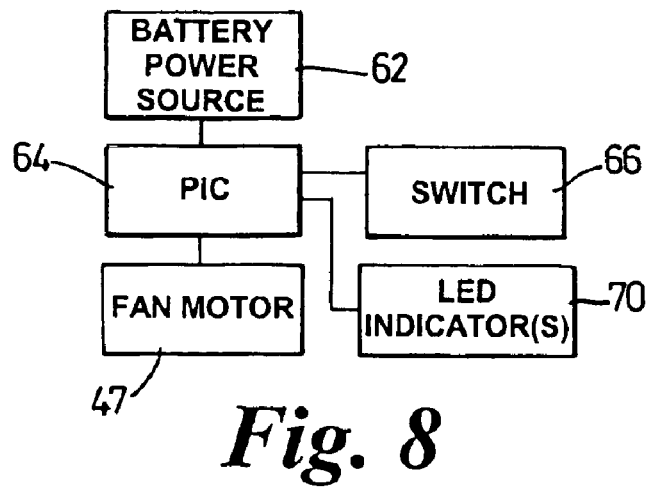
FIG. 8 is a schematic diagram of a control system for the goggle of FIG. 1.

Referring to FIG. 6, a power module 60 for the fan 46 is mounted inside the body 14 to one side of the inlet plenum channel 42, just below the ocular chamber 34. The power module 60 contains batteries 62 for powering the fan 46, control electronics in the form of an integrated circuit board 64 for controlling the speed of the fan 46 and a tactile switch 66 that allows the wearer to turn the fan on and off and adjust the speed of the fan when it is running. A power lead 68 connects the power module 60 to the fan motor 47. The power module 60 also has an LED 70 within it, and a light guide 72 extends upwards from the power module 60 through the gasket 30 into the ocular chamber 34 where its upper end 74 provides a visual indicator to the wearer. FIG. 8 shows the components of the fan drive system in the form of a block diagram.

Referring to FIGS. 1, 3, 4 and 5, when the fan 46 is running, air is drawn into the inlet chamber 44 as indicated by the arrows A and through the fan chamber 51 past the fan 46, and then is directed upwards from the back 51 of the fan chamber by the deflector plate 54 up the upper part 42a of the plenum channel 42 into the ocular chamber 34. When it reaches the ocular chamber 34, it exits the top 42b of the plenum channel 42, traveling upwards and outwards across the inner surface 12a of the lens 12 as shown by arrows B. As can be seen most clearly in FIGS. 1 and 5, because the plenum channel 42 is arched over the wearer's nose, the air B spreads across the lens 12 in fan-shaped path, traveling over substantially the whole area of the lens 12. When it reaches the top of the lens, it exits through the outlet apertures 34b in the top of the ocular chamber 34, as shown by arrows D. Because the outlet from the plenum channel 42 and the apertures 34b in the top of the ocular chamber are close to, and in fact directly adjacent to, the lens 12, the air B travels up the inner surface of the lens 12 in a laminar flow layer. The total cross-sectional area of the apertures 34b is made greater than the area of the outlet of the plenum channel 42 so that there is no buildup of pressure in the ocular chamber, and so as to encourage the smooth laminar flow of air across the lens 12. The speed of the fan 42 is also controlled so that the air speed across the lens remains low enough for the laminar flow to remain stable. This is so that turbulent flow, which can result in air being directed towards the wearer's eyes, is avoided. A further advantage of this thin layer of laminar flow is that it produces a lower pressure region in the ocular chamber adjacent to the lens, and this tends to draw air away from the wearer's face 32, as shown by arrows C, into the upward flow and out through the top of the ocular chamber 34. This aids in the evaporation and removal of sweat from the wearer's face. A further advantage of the upward flow across the lens is that convection caused by heat from the wearer's face contributes to the upward flow and does not disturb the smooth laminar flow.

Figure 4:
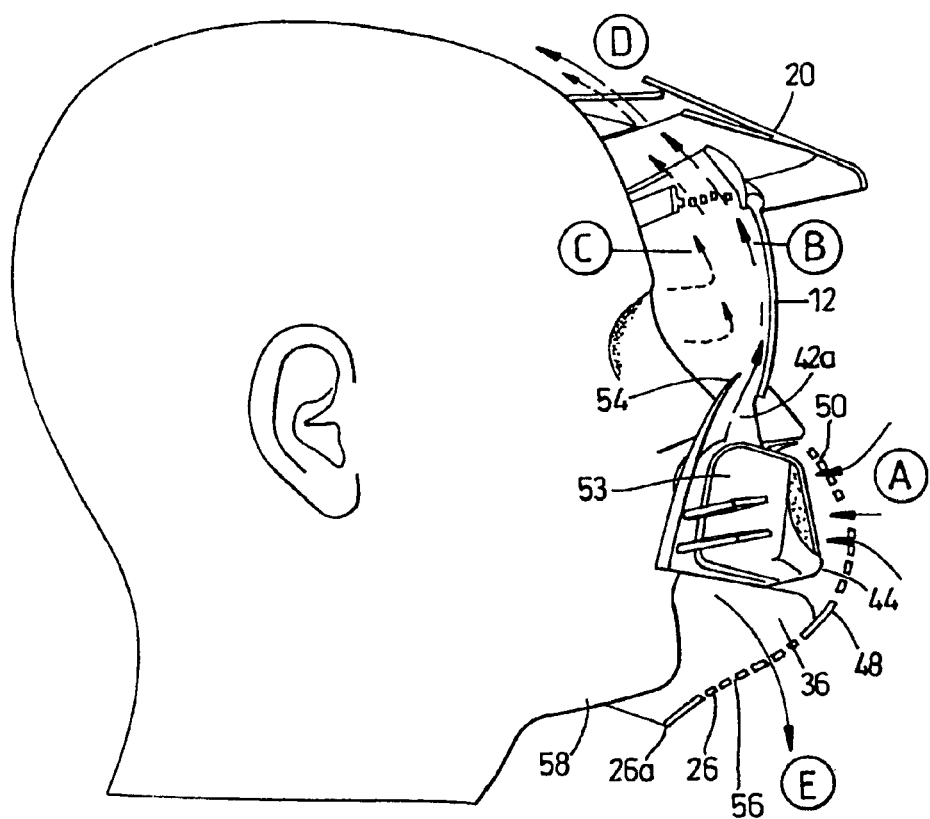
FIG. 4 is a partially cut-away side view of the goggle of FIG. 1.
Figure 5:
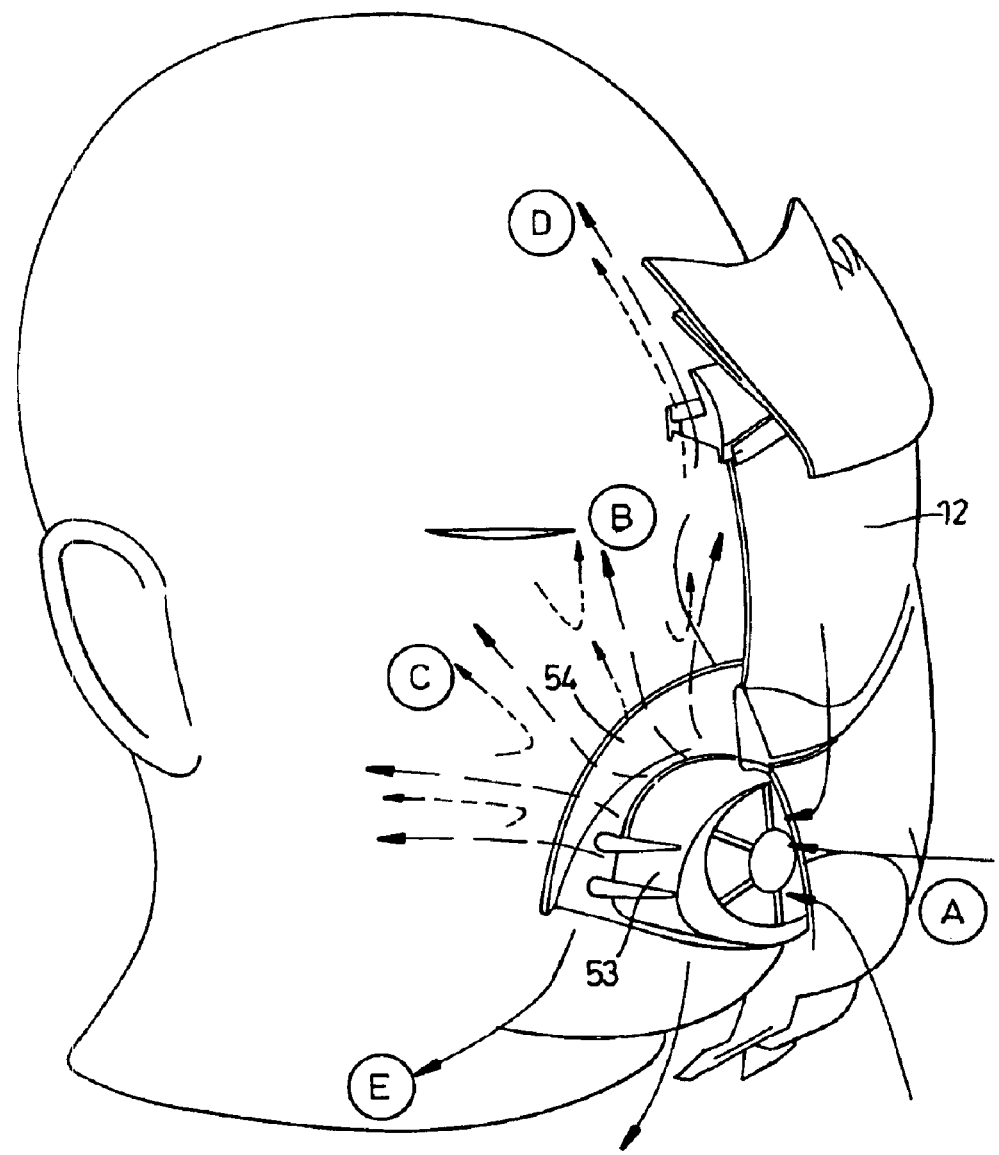
FIG. 5 is a partially cut-away front perspective view of the goggle of FIG. 1.

As can best be seen in FIGS. 3 and 4, the flow of air to and from the wearer's mouth 38 and nose 40 as he breathes is through the exhalation chamber 36 and through the apertures 56 in the jaw protection portion 26 of the goggle, as well as between the very bottom edge 26a of the goggle and the wearer's jaw 58. Because these apertures are in the lower part of the goggle and face in a generally downward direction, air exhaled by the wearer is generally directed downwards away from the goggle, as shown by arrows E, and therefore also away from the inlet 44 which is in the front of the goggle facing in a generally forward direction. This means that the moisture in the wearer's breath is directed away from the inlet 44 to the plenum channel 42 and therefore tends not to enter the ocular chamber 34, which is beneficial in avoiding fogging of the lens 12.

Figure 7:
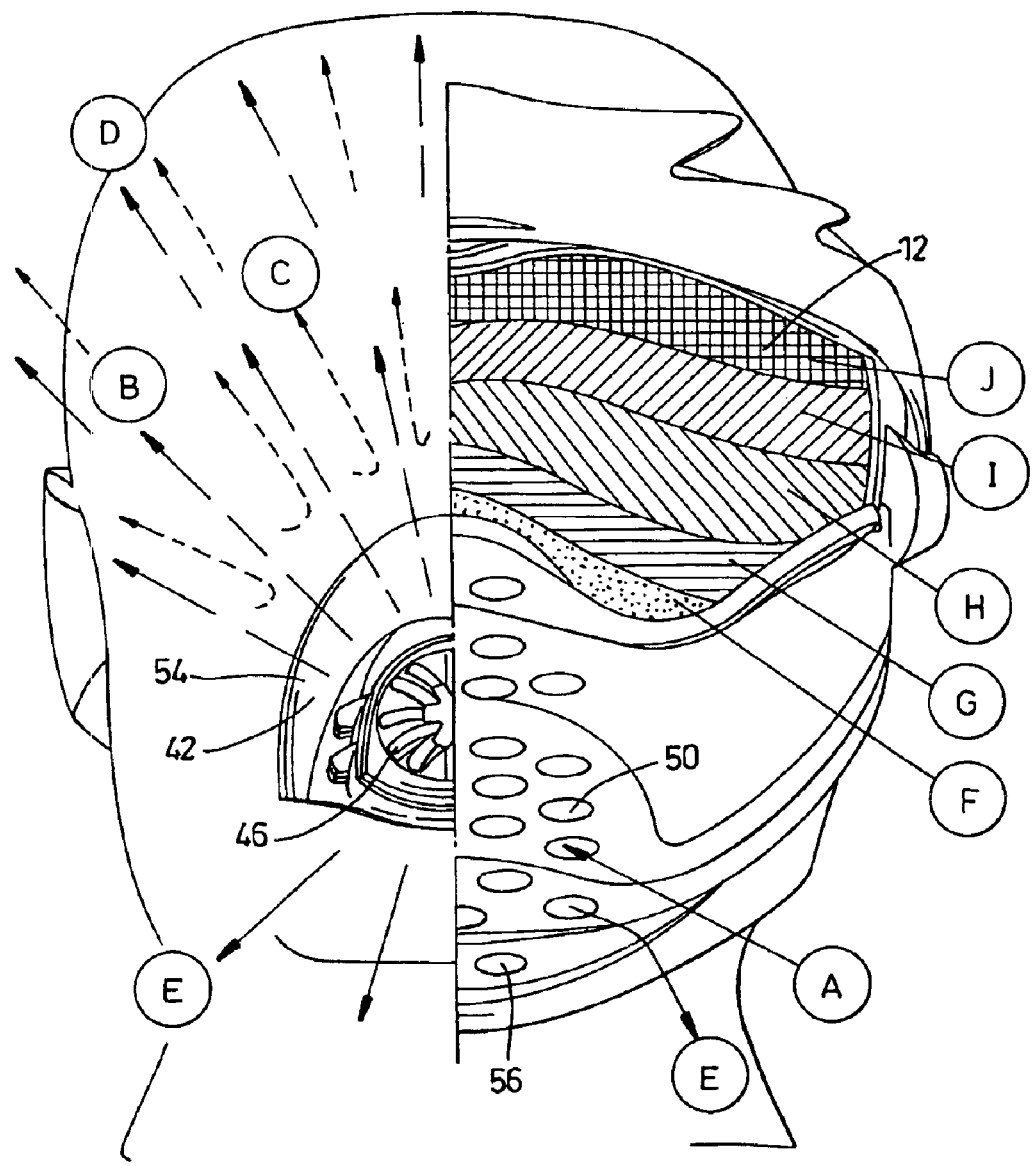
FIG. 7 is a further partially cut-away view of the goggle of FIG. 1.

Referring to FIG. 7, as the air B spreads upwards across the lens 12, it clears any fogging from the lens in regions F, G, H, I, J, which are at increasing distance from the outlet of the plenum channel 42. Therefore, the region F at the lowest part of the lens 12 arched around the nose 40 of the wearer clears first, as it is closest to the outlet of the plenum channel 42. The regions then clear in order until the topmost region J, which extends across the top of the lens 12 closest to the apertures 34b. The steady laminar flow of air over the lens ensures that the fogging always clears in this regular manner.

Figure 9:
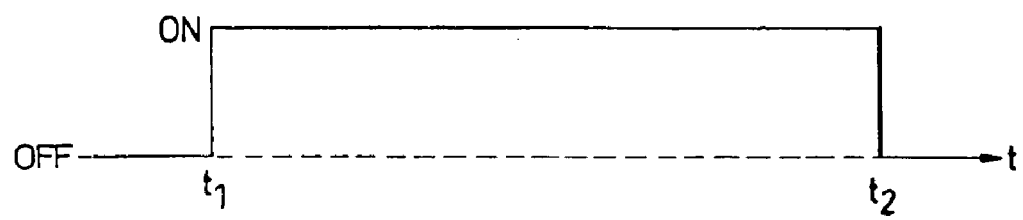
FIGS. 9, 10 and 11 are schematic diagrams showing the drive current of a fan motor forming part of the goggle of FIG. 1 under various conditions.
Figure 10:
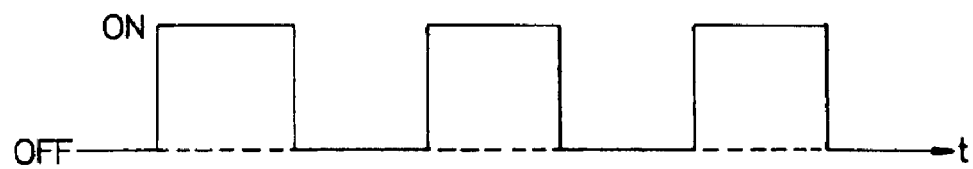
Figure 11:
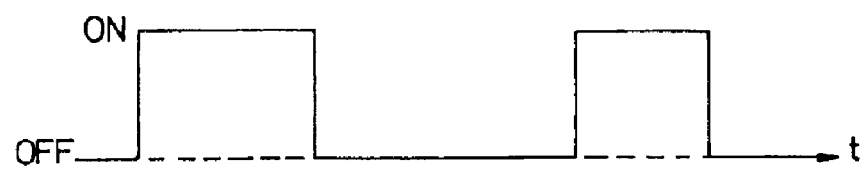

Referring to FIG. 9, in its simplest form the control electronics 64 controls the fan 46 between an off state and an on state. FIG. 9 shows how the drive current to the fan motor 47 can be turned on at time $t_1$ and off again at time $t_2$. The motor could simply be turned on and off in response to the wearer's operation of the switch 66. However, in this embodiment the control electronics 64 are arranged to pulse the fan on and off as shown in FIG. 10. Each time the fan is turned on, it is kept on for at least a minimum on time, which in this case is on the order of one or two seconds, which is long enough to allow the flow of air across the lens 12 to build up and settle in the steady state laminar flow. This ensures that the fan can operate under optimum conditions. Between each on time the fan is turned off. The on and off times are controlled to the optimum length, which in this embodiment is fixed, to produce a satisfactory speed of clearing of the lens without producing too rapid a drain on the power of the batteries 62. The exact timing of the switching on and off of the motor can be varied in a number of ways depending on the type of goggle and the circumstances under which it is expected to be used. For example, it can be turned on for a single continuous period of predetermined length when first switched on by the switch 66 so as to clear the lens 12 as rapidly as possible, and then switch to a pulsing on and off to keep the lens 12 clear but preserve battery power.

While the fan is switched on at the switch 66, the control module 60 keeps the LED 70 switched on, which is visible to the wearer through the light guide 74 as an indicator that the fan is switched on. This is particularly useful where the fan motor 47 is a quiet brushless motor, such as an induction motor, in which case it can be hard for the wearer to tell whether the fan is running or not, particularly if the goggle is being worn in a noisy environment.

Figure 12:
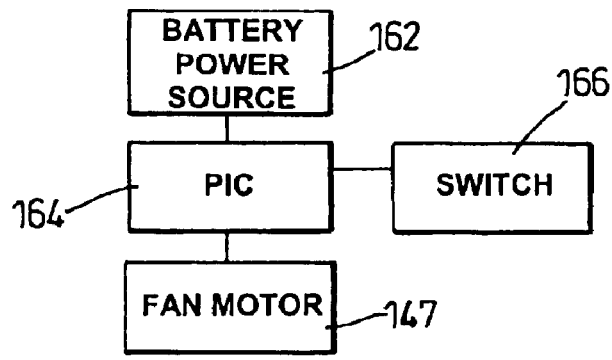
FIG. 12 is a schematic diagram of a control system for a goggle according to a second embodiment of the invention.

Referring to FIG. 12, in a second embodiment of the invention the fan control system includes control electronics 164, a battery 162, a switch 166 and a fan motor 147, but the LED is omitted.

Figure 13:
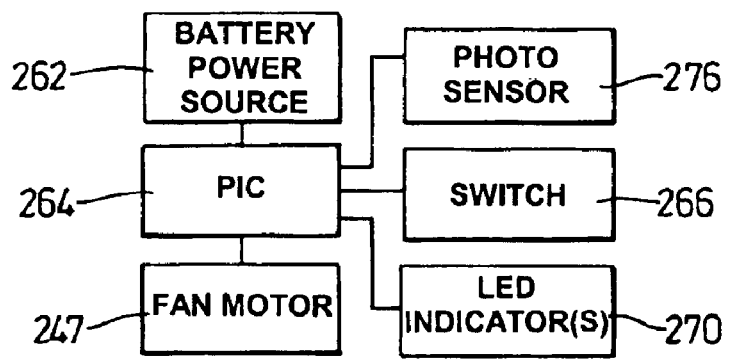
FIG. 13 is a schematic diagram of a control system for a goggle according to a third embodiment of the invention.

Referring to FIG. 13, in a third embodiment the motor control system includes all of the components of the first embodiment, which are indicated by the same reference numeral increased by 200, but further includes a photo sensor 260 mounted at a suitable position on the goggle body 16 to detect the ambient light level. The control electronics 264 then use the signal from the photo sensor 260 to control the level of light produced by the LED 270 so as to be at a suitable level relative to the ambient light.

Figure 14:
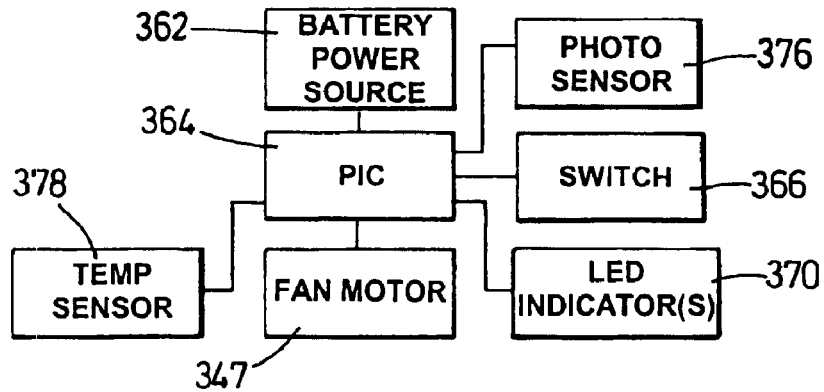
FIG. 14 is a schematic diagram of a control system for a goggle according to a fourth embodiment of the invention.

Referring to FIG. 14, in a fourth embodiment of the invention the fan control system includes all of the features of the third embodiment, indicated by the same reference numerals but increased by a further 100, and also includes a temperature sensor 378 mounted on the goggle body 16 inside the ocular chamber 34. The temperature sensor 378 sends signals to the control electronics 364 indicative of the temperature in the ocular chamber 34, and the control electronics 364 vary, and control, the length of the on and off time pulses of the motor 347 in response to changes in the measured temperature. Since fogging occurs when the air within the ocular chamber 34 reaches its dew point due to either falling temperature or increasing humidity, the fan 46 is controlled so as to increase the airflow across the lens 12 as the temperature falls. This can conveniently be done by controlling the off time between pulses of power to the fan 46, and optionally also the length of the on time pulses.

The exact position of the temperature sensor 378 is important in determining the system's effectiveness in anticipating fogging. Preferably, it is mounted on or very near to the lens 12, as the most common cause of fogging is cooling of the air in the ocular chamber 34 by the lens 12.

Figure 15:
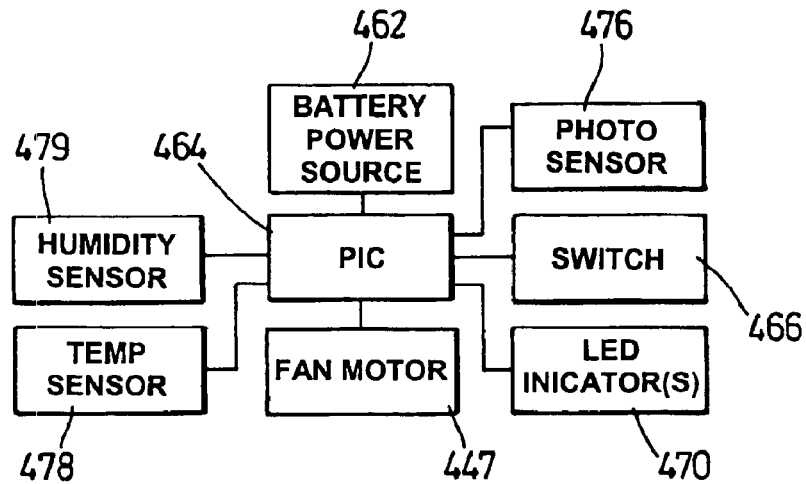
FIG. 15 is a schematic diagram of a control system for a goggle according to a fifth embodiment of the invention.

With reference to FIG. 15, in a fifth embodiment of the invention the fan control system includes all of the features of the fourth embodiment, indicated by the same reference numerals but increased by a further 100, and also includes a humidity sensor 479 mounted on the goggle body 16 within the ocular chamber 34. This sends signals to the control electronics 464 indicative of the humidity of the air within the ocular chamber 34. The control electronics respond by increasing the amount of air blown across the lens 12 in response to an increase in humidity.

Figure 16:
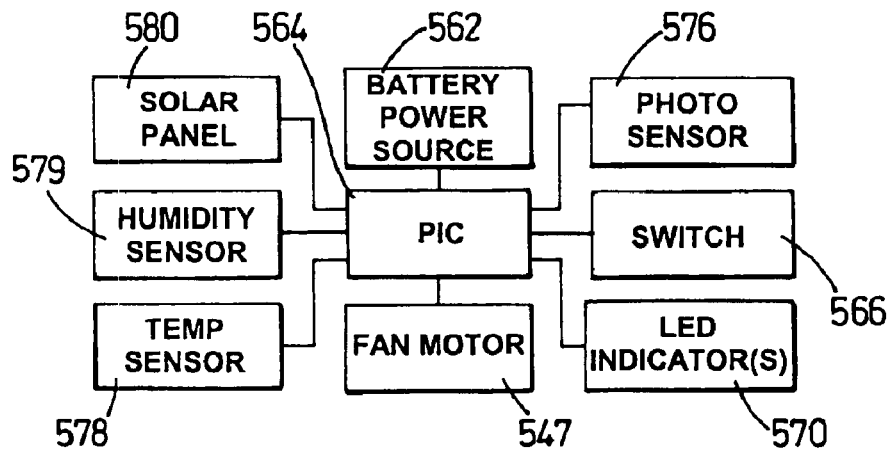
FIG. 16 is a schematic diagram of a control system for a goggle according to a sixth embodiment of the invention.

Finally, referring to FIG. 16, in a sixth embodiment of the invention the fan control system includes all of the features of the fifth embodiment, indicated by the same reference numerals but increased by a further 100, and also includes a panel of solar cells 580. The solar panel 580 can be mounted on the exterior of the goggle body 16, or alternatively on the interior of the ocular chamber 34—for example, along the bottom of the ocular chamber to either side of the plenum channel 42, where it will be protected by the lens 12. The solar panel 580 produces electrical power, which is either used directly to drive the fan or stored in the battery 546, under the control of the control electronics 564.

Referring back to FIG. 2, the strap 16 is connected to the goggle body 14 by means of pivoting connectors 90 which each include a tag 92 pivotingly mounted on a support 94 so that it can pivot about an axis which is, when in use with the wearer's head upright, substantially horizontal and transverse to the goggle. The strap is connected at each end to one of the tags 92 so that when the strap 16 is moved up and down the back of the wearer's head 18, the angle of the strap 16 can change relative to the body 14 without tending to tilt the body 14 on the wearer's face. The visor 20 is pivotably mounted on the same supports 94 so that it can be pivoted up and down to vary the amount of shading it provides for the user's eyes. The strap 16 is made of a strip of molded elastomeric material having a number of perforations or apertures 96 through it which are formed with soft curved edges so as to avoid tearing stress points. The apertures 96 are in two parallel rows along the strap. The apertures 96 through the strap 16 serve a number of purposes. They allow the strap 16 to stretch easily to fit the wearer's head 18, in this embodiment to a sufficient degree to avoid the need for an adjustment buckle altogether. This nonadjustability makes the strap 16 more comfortable and easier to use than conventional straps. Also, the apertures 96 allow perspiration forming on the wearer's head 18 to evaporate more easily, as they reduce the amount of surface area of the wearer's head which is covered. For this reason it is desirable that the apertures 96 take up a relatively large proportion of the area of the strap, in this case approximately half of its total surface area. Furthermore, the use of elastomeric material for the strap 16 prevents the propagation of bacteria in the strap, thereby avoiding unpleasant odors, and obviates the need for silicone beading used on conventional fabric straps.

Figure 17:
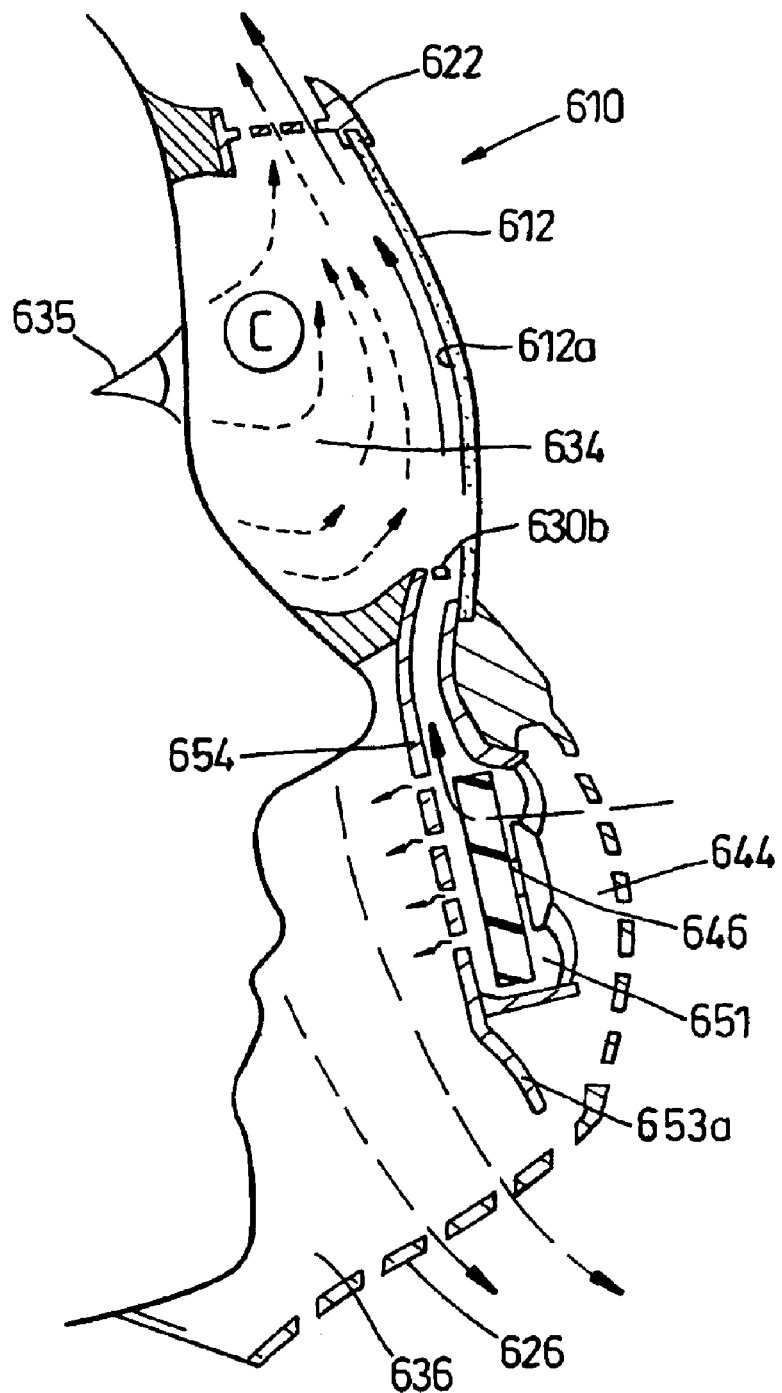
FIG. 17 is a section similar to FIG. 3 through a goggle according to an eighth embodiment of the invention.

Referring to FIG. 17, a seventh embodiment of the invention, a goggle system 610 is designed to be similar to the first embodiment of FIGS. 1 through 7, with corresponding parts indicated by the same reference numerals preceded by a 6. In this embodiment, the exhalation chamber 636, while being separate from the ocular chamber 634, and the fan chamber 644, is not sealed off from them. Limited air flow can therefore occur between the chambers, but the air pressures in chambers 634, 636, 644 produced by the fan 646 are such that the airflow does not significantly affect the defogging of the lens 612.

The diverter plate 654 has a number of small apertures 654a through it behind the fan 646 to allow some airflow from the inlet chamber 644 into the exhalation chamber. This helps to provide a continuous supply of fresh air for the wearer to breathe. However, the apertures 654a are small enough to ensure that the majority of the air from the inlet chamber 644 is diverted upwards onto the inner surface 612a of the lens 612. Also, because the fan 646 creates a region of high pressure in the back 652 of the inlet chamber 644, this region will generally be at a higher pressure than the exhalation chamber 636, and air exhaled by the wearer will generally not be able to pass from the exhalation chamber forward through the diverter plate 654 into the inlet chamber 644.

A deflecter 653a extends downward from the fan chamber wall 53 toward the jaw protection portion 626 of the goggle 610, but stops short of the jaw protection portion 626 so that a small opening 653b is left between them. This deflecter 653a acts to deflect exhaled air downward away from the inlet chamber 644, and therefore serves the same function as the web 53a of FIG. 3, but without forming a total seal between the exhalation chamber 636 and the inlet chamber 644. In this case, it is the shape of the deflecter 653a and the direction of flow of the exhaled air which ensure that no significant amount of exhaled air passes into the inlet chamber 644.

At the lower edge of the lens 612, a grille 630b is formed in the lens frame portion 622. This grille extends across the whole of the lower edge of the lens 612, and over the top of the plenum channel 42, where it opens into the ocular chamber 634. The grille 630b comprises a plastic molding with a number of small apertures through it. At the sides of the goggle, to either side of the diverter plate 653, the grille 630b provides limited communication between the ocular chamber 34 and the exhalation chamber 636. However, as the fan blows air up into the ocular chamber, the pressure in the ocular chamber 634 is higher than in the exhalation chamber 636, so air tends to flow down from the ocular chamber 634 into the exhalation chamber 636 and not in the opposite direction.

It will be appreciated that preferred embodiments of the invention can successfully control a number of factors to reduce fogging of the goggle lens. The airflow distribution across the lens can be controlled to provide rapid and uniform defogging and the nonturbulent air flow within the ocular chamber helps to prevent air flowing across the ocular region, causing dryness of the eye and leading to irritation. These are both achieved by control of the fan speed and airflow direction. Also, the selection of a suitable fan and motor helps to keep noise to a minimum.

What is claimed is:

1. A goggle comprising a lens, a body structure supporting the lens and defining therewith an ocular chamber for extending over the eyes of a wearer, wherein the body structure further defines: an exhalation chamber for extending over at least one of the nose and mouth of a wearer and an inlet chamber at least part of which is arranged to be in front of the exhalation chamber in use; the goggle further comprising a fan located in the inlet chamber, and air deflection means located between the inlet chamber and the exhalation chamber and arranged to deflect air from the fan upwards into the ocular chamber.

2. A goggle according to claim 1, wherein the air deflection means is constructed and arranged to direct air across the inner surface of the lens in an upward direction.

3. A goggle according to claim 2, wherein the body structure defines an ocular chamber outlet at the upper side of the ocular chamber through which air entering the ocular chamber from the inlet chamber can escape from the ocular chamber.

4. A goggle according to claim 1, wherein the body structure defines an ocular chamber outlet at the upper side of the ocular chamber through which air entering the ocular chamber from the inlet chamber can escape from the ocular chamber.

5. A goggle according to claim 4, wherein the outlet has a covering thereover having apertures therethrough which are no greater than 30 mm$^2$, so as to prevent debris from entering the ocular chamber.

6. A goggle according to claim 4, wherein the ocular chamber outlet is positioned adjacent to the lens so that air flowing across the lens can flow on through the ocular chamber outlet.

7. A goggle according to claim 1, wherein the inlet chamber has an inlet through which air can enter the inlet chamber from the exterior of the goggle.

8. A goggle according to claim 7, wherein the inlet chamber is formed in the front of the goggle.

9. A goggle according to claim 1, wherein the fan is positioned in a part of the inlet chamber in front of the exhalation chamber.

10. A goggle according to claim 1, wherein the fan is positioned so as to be, while in use, in front of the wearer's nose or mouth.

11. A goggle according to claim 1, wherein the exhalation chamber has at least one exhaled air outlet for exhaled air.

12. A goggle according to claim 11, wherein the inlet chamber has an inlet through which air can enter the inlet chamber from the exterior of the goggle, and wherein the exhaled air outlet is arranged to be, while in use, below the inlet.

13. A goggle according to claim 12, wherein the exhaled air outlet is arranged to direct exhaled air downward, away from the inlet chamber.

14. A goggle according to claim 11, wherein the inlet is formed in the front of the goggle, and wherein the exhaled air outlet is arranged to be, while in use, below the inlet.

15. A goggle according to claim 11, wherein the exhaled air outlet is arranged to direct exhaled air downward away from the inlet chamber.

16. A goggle according to claim 15, wherein the channel outlet is arranged to direct air in a direction substantially parallel to the lens so that the air flows across the inner surface of the lens.

17. A goggle according to claim 1, wherein the deflection means partly defines a channel between the inlet chamber and the ocular chamber, the channel having an outlet which is adjacent to the lens.

18. A goggle according to claim 1, wherein the deflection means is arranged to direct the air so that it flows across the lens in a substantially laminar manner.

19. A goggle according to claim 1, wherein the air deflection means is arranged to direct the airflow in the ocular chamber to occur mostly in a region of the ocular chamber adjacent to the lens and spaced away from the wearer's face.

20. A goggle according to claim 1 and further comprising a partition between the ocular chamber and the exhalation chamber to inhibit the flow of air from the exhalation chamber to the ocular chamber.

21. A goggle according to claim 20, wherein the partition is sealed to prevent the flow of air from the exhalation chamber to the ocular chamber.

22. A goggle according to claim 20, wherein the partition defines at least one opening through which air can flow from the ocular chamber to the exhalation chamber.

23. A goggle according to claim 1, wherein the air deflection means comprises at least part of a partition between the inlet chamber and the exhalation chamber to inhibit the flow of air from the exhalation chamber to the inlet chamber.

24. A goggle according to claim 23, wherein the partition between the inlet chamber and the exhalation chamber is sealed to prevent the flow of air from the exhalation chamber to the inlet chamber.

25. A goggle according to claim 23, wherein the partition between the inlet chamber and the exhalation chamber defines at least one opening through which air can flow from the inlet chamber to the exhalation chamber.

26. A goggle according to claim 25, and further comprising sensing means includes a temperature sensor arranged to measure the temperature in a region within the goggle, close to the lens.

27. A goggle according to claim 23, and further comprising a drive system includes a sensing means arranged to sense a condition which will affect fogging of the lens, and the controller is arranged to control operation of the fan in response to a signal from the sensing means.

28. A goggle according to claim 1 and further comprising a strap formed from a piece of elastomeric material.

29. A goggle according to claim 28, wherein the strap has a plurality of apertures formed therethrough.

30. A goggle according to claim 28, wherein the strap is non-adjustable.

31. A goggle according to claim 28, wherein the strap is arranged to pass around the back of the wearer's head.

32. A goggle according to claim 1, wherein the body structure is of a flexible construction, thereby being arranged to follow the contours of a wearer's face.

33. A goggle comprising a lens, a body structure supporting the lens and defining an air inlet means arranged to direct air from the exterior of the goggle across an inner surface of the lens, a fan located in the air inlet means for causing air to flow through the air inlet means, and a drive system for driving the fan wherein the drive system includes a controller arranged to switch the fan repeatedly between an on state and an off state so as to control the amount of air directed across the lens, and to control the timing of the switching so that each time the fan is switched to the on state it remains in that state for at least a predetermined time to allow for air flow across the lens to reach a steady state.

34. A goggle according to claim 33, wherein the controller is arranged to vary the length of the periods for which the fan is in at least one of the on state and the off state so as to vary the amount of air flow across the lens.

35. A goggle according to claim 33, wherein the drive system includes a sensing means arranged to sense fogging of the lens, and the controller is arranged to control operation of the fan in response to a signal from the sensing means.

36. A goggle according to claim 35, wherein the sensing means includes a temperature sensor arranged to measure the temperature in a region within the goggle, close to the lens.

37. A goggle according to claim 35, wherein the sensing means includes a humidity sensor arranged to measure the humidity of air in a region within the goggle, close to the lens.

38. A goggle according to claim 33, and further comprising sensing means includes a humidity sensor arranged to measure the humidity of air in a region within the goggle, close to the lens.

39. A goggle comprising a lens, a body structure supporting the lens and defining an air inlet means arranged to direct air from the exterior of the goggle across an inner surface of the lens, a fan located in the air inlet means for causing air to flow through the air inlet means, and a drive system for driving the fan wherein the drive system includes a sensing means arranged to sense fogging of the lens, and a controller arranged to control operation of the fan response to a signal from the sensing means.

40. A goggle according to claim 39, wherein the strap is connected to the body structure by means of pivoting connectors.

41. A goggle according to claim 39, wherein the strap has a plurality of apertures formed therethrough.

42. A goggle according to claim 34, wherein the strap is non-adjustable.

43. A goggle according to claim 39, wherein the strap is arranged to pass around the back of a wearer's head.

* * * * *